United States Patent
Gleich et al.

(10) Patent No.: US 8,188,732 B2
(45) Date of Patent: May 29, 2012

(54) ARRANGEMENT AND METHOD FOR INFLUENCING MAGNETIC PARTICLES IN A REGION OF ACTION USING DISTINGUISHABLE MAGNETIZATION OF THE TWO MAGNETIC PARTICLES

(75) Inventors: Bernhard Gleich, Hamburg (DE); Juergen Weizenecker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 383 days.

(21) Appl. No.: 12/519,628

(22) PCT Filed: Dec. 17, 2007

(86) PCT No.: PCT/IB2007/055158
§ 371 (c)(1),
(2), (4) Date: Jun. 17, 2009

(87) PCT Pub. No.: WO2008/078262
PCT Pub. Date: Jul. 3, 2008

(65) Prior Publication Data
US 2010/0033172 A1 Feb. 11, 2010

(30) Foreign Application Priority Data
Dec. 20, 2006 (EP) .................................. 06126581

(51) Int. Cl.
*G01R 33/12* (2006.01)
*G01N 27/72* (2006.01)
(52) U.S. Cl. ........... 324/228; 324/243; 600/12; 128/899
(58) Field of Classification Search .................. 324/228, 324/243; 600/12; 128/899
See application file for complete search history.

(56) References Cited

U.S. PATENT DOCUMENTS

| 4,639,674 A * | 1/1987 | Rippingale .................... 324/326 |
| 4,878,023 A * | 10/1989 | Overweg et al. .............. 324/318 |
| 4,963,694 A | 10/1990 | Alexion et al. |
| 7,167,004 B1 * | 1/2007 | Kruip ............................ 324/320 |
| 2001/0031906 A1 * | 10/2001 | Ishikawa et al. ................ 600/13 |
| 2003/0085703 A1 * | 5/2003 | Gleich .......................... 324/309 |

FOREIGN PATENT DOCUMENTS

| DE | 10151778 | 5/2003 |
| EP | 1145738 | 10/2001 |
| EP | 1304542 | 4/2003 |

OTHER PUBLICATIONS

Gleich, et al., "Magnetic Particle Imaging (MPI)", Medicamundi, Philips Medical Systems, Shelton, CT, US, vol. 50, No. 1, May 1, 2006, pp. 66-71.
Kim, et al., "Time-Resolved Observation of Barkhausen Avalanche in Co thin Films Using Magneto-Optical Microscope Magnetometer", Journal of Applied Physics, American Institute of Physics, New York, US, vol. 93, No. 10, May 15, 2003, pp. 6564-6566.
Sullivan, "Optimal Choice for Number of Strands in a Litz-Wire Transformer Winding", IEEE Transactions on Power Electronics, IEEE Service Center, Piscataway, NJ, US, vol. 14, No. 2, Mar. 1, 1999, pp. 283-291.

* cited by examiner

*Primary Examiner* — Jay Patidar

(57) ABSTRACT

An arrangement and a method for influencing and/or detecting and/or locating magnetic particles in a region of action include a driver generating a magnetic drive field so that magnetization of the magnetic particles changes. The magnetic particles include first and second magnetic particles. The arrangement further include a receiver having a first receiving probe providing a first signal and a second receiving probe providing a second signal. A detector determines signal features arising from the first particle in the first signal and in the second signal.

19 Claims, 3 Drawing Sheets

ARRANGEMENT AND METHOD FOR INFLUENCING MAGNETIC PARTICLES IN A REGION OF ACTION USING DISTINGUISHABLE MAGNETIZATION OF THE TWO MAGNETIC PARTICLES

CROSS REFERENCE TO RELATED APPLICATIONS

This application claims the benefit of EP provisional application s/n 06126581.5, filed Dec. 20, 2007, which is incorporated herein by reference. Related applications are PCT s/n IB2007/055126, "Arrangement and Method for Influencing and/or Detecting Magnetic Particles in a Region of Action," filed Dec. 14, 2007, PCT s/n IB2007/055152, "Arrangement for Influencing and/or Detecting Magnetic Particles in a Region of Action and Method of Producing a Disk Shaped Coil," filed Dec. 17, 2007, PCT s/n IB2007/055157, "Arrangement and Method for Influencing and/or Detecting Magnetic Particles in a Region of Action," filed Dec. 17, 2007, PCT s/n IB2007/055134, "Arrangement and Method for Influencing and/or Detecting Magnetic Particles in a Region of Action," filed Dec. 14, 2007, PCT s/n IB2007/055174, "Arrangement and Method for Influencing and/or Detecting Magnetic Particles in a Region of Action," filed Dec. 17, 2007, PCT s/n IB2007/055131, "Arrangement and Method for Influencing and/or Detecting Magnetic Particles in a Region of Action," filed Dec. 14, 2007, PCT s/n IB2007/055162, "Method and Arrangement for Locating Magnetic Markers in a Region of Action," filed Dec. 17, 2007, PCT s/n IB2007/055178, "Arrangement and Method for Detecting and/or Locating a Magnetic Material in a Region of Action, Use of a Arrangement In the Examination of Buildings," filed Dec. 17, 2007, PCT s/n IB2007/055177, "Method and Arrangement for Influencing and/or Detecting Magnetic Particles in a Region of Action," filed Dec. 17, 2007, PCT s/n IB2007/055204, "Method and Arrangement for Separating Magnetic Particles, Magnetic Particles and Use of Magnetic Particles," filed Dec. 18, 2007, PCT s/n IB2007/055165, "Arrangement and Method for Influencing and/or Detecting Magnetic Particles in a Region of Action, Coil Arrangement," filed Dec. 17, 2007, and PCT s/n IB2007/055163, "Influencing and/or Detecting Magnetic Particles in a Region of Action of a Examination Object," filed Dec. 17, 2007.

The present invention relates to an arrangement for influencing and/or detecting and/or locating magnetic particles in a region of action. Furthermore, the invention relates to a method for influencing and/or detecting and/or locating magnetic particles and to the use of magnetic particles.

An arrangement of such a kind is known from German patent application DE 101 51 778 A1. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement and such a method have the advantage that it can be used to examine arbitrary examination objects—e. g. human bodies—in a non-destructive manner and without causing any damage and with a high spatial resolution, both close to the surface and remote from the surface of the examination object.

Nevertheless, the overall setup of such an arrangement has the substantial drawback that only magnetization signals of such magnetic particles are accessible to the receiving means which are located in or near the first sub-zone of the region of action. In other words, the overall setup of the known arrangement limits the interaction of the magnetic particles with the drive field to a defined space ("field of view") at the first sub-zone or near the first sub-zone, thereby limiting the covering of the field of view. A further drawback of the known arrangement lies in the fact that for very high resolutions of e.g. better than 10 µm, the selection field moves the magnetic particles out of the field of view.

It is therefore an object of the present invention to provide an arrangement partially similar to the arrangement mentioned initially, in which the drawbacks of the prior art are avoided or at least reduced.

The above object is achieved by an arrangement for influencing and/or detecting and/or locating magnetic particles in a region of action, wherein the arrangement comprises drive means for generating a magnetic drive field so that the magnetization of the magnetic particles changes, wherein the magnetic particles comprise at least a first magnetic particle, the arrangement further comprising receiving means for acquiring signals, which signals depend on the magnetization of the first magnetic particle in the region of action, the receiving means comprising at least a first receiving probe providing a first signal and a second receiving probe providing a second signal, the arrangement further comprising detection means for determining signal features arising from the first magnetic particle in the first signal and in the second signal.

The advantage of such an arrangement is that potentially a larger part of the region of action or the totality of the region of action is taken continuously into consideration when conducting a measurement with the inventive arrangement and/or according to the inventive method. According to the present invention, the power of spatial resolution when locating magnetic particles and the quality of locating the magnetic particles depends on the one hand on the number of the magnetic particles, their size and/or their density in respect of a given volume of the region of action and on the other hand on the configuration or the mode of operation of the receiving means of the arrangement and their power of temporal resolution of the signals recorded by the receiving means. According to the present invention, it is the different magnetization responses of the different magnetic particles inside the, e.g. oscillating, magnetic drive field that are used to differentiate or to distinguish the individual or particular magnetic particles. The different magnetization responses are also called signal features. Especially, the different magnetization responses of the different magnetic particles inside the magnetic drive field are provided as Barkhausen jumps (abrupt changes of the magnetization of at least the first and/or the second magnetic particle), but other physical effects leading to distinguishable magnetization responses of the different particles can also be used according to the present invention. The different magnetization responses of the different magnetic particles are more or less deterministic for each particle but in general quite stochastic for different particles. According to the present invention, it is possible to compare the different magnetization responses in different signals recorded in parallel by the receiving means such that the location of each magnetic particle can be reconstructed due to the fact that the different magnetization responses are in general separated in the time domain of the recorded signals. The detection means are preferably provided such that a signal processing unit compares the different signals of the different receiving probes such that the signal features and therefore the different particles can be determined. According to a preferred embodiment of the present invention, the localization of the first magnetic particle depends on the amplitude of the signal features in the first signal and in the second signal. The different strength (or amplitude) of the different magnetization responses in the signals of different receiving probes (positioned at different locations relative to the magnetic particles) allows the determination of the position of the individual particle if the signal features of that particle are detectable. Thereby, due to the fact that the magnetization of the first magnetic particle and of the second magnetic particle is distinguishable due to, e.g., Barkhausen jumps induced by the magnetic drive field, it is possible localize the individual magnetic particles.

Furthermore, it is preferred that the magnetization of the first magnetic particle and of the second magnetic particle is distinguishable in the time domain and/or that the receiving means comprise a multitude of receiving probes. It is thereby advantageously possible to distinguish a multitude of different magnetic particles.

According to a preferred embodiment of the present invention, the first receiving probe and the second receiving probe are positioned such that by comparing the first signal and the second signal, information about the spatial relationship of the first magnetic particle and the second magnetic particle relative to the first receiving probe and the second receiving probe is accessible. Advantageously, it is thereby possible to provide the possibility to individually locate the magnetic particles with a relatively good spatial resolution. This is due to the fact that a magnetic particle located nearer to the first receiving probe than to the second receiving probe will normally (i.e. with identical conditions in other respects) induce a stronger magnetization response in the first signal (the signal provided by the first receiving probe) than in the second signal (the signal provided by the second receiving probe).

According to still a further embodiment of the present invention, the arrangement comprises selection means for generating a magnetic selection field having a pattern in space of its magnetic field strength such that a first sub-zone having a low magnetic field strength and a second sub-zone having a higher magnetic field strength are formed in the region of action. Thereby, it is advantageously possible according to the present invention that the magnetic field experienced by the different individual magnetic particles to be localized can be changed such that the portion of the region of action where only the magnetic drive field is present (and no supplementary magnetic field) is reduced such that the number of individual magnetic particles to localize is sufficiently small that it is possible to separate the individual magnetization responses of these particles in the time domain of the signal delivered by the receiving probes. Without such a magnetic selection field (and thereby the generation of the first sub-zone of the region of action where a comparably low magnetic field strength is present in comparison to the second sub-zone of the region of action where (the absolute value of) the magnetic field strength is higher) and in a situation where too many individual magnetic particles are to be localized such that the separation in the time domain of the signals delivered by the receiving probes is not possible anymore, no correct localization of the magnetic particles is possible. For example, this is the case in the situation where too many magnetic particles generate their magnetization response due to the applied exterior magnetic field (e.g. a homogeneous magnetic drive field) at the same time, i.e. for example the Barkhausen jumps occur almost simultaneously. The (normally inhomogeneous, especially gradient like formed) magnetic selection field which is superposed on the (normally homogeneous) magnetic drive field changes the spatial distribution of the exterior magnetic field that the different magnetic particles experience. Therefore, by applying the magnetic selection field, it is possible to change the moment of occurrence of the Barkhausen jumps for a subset of the individual particles under investigation (corresponding more or less to those magnetic particles located inside the second sub-zone of the region of action) such that the time domain signals delivered by the receiving probes are less crowded (due to a smaller number of magnetic particles in or near the first sub-zone of the region of action) and the magnetization responses of the magnetic particles in or near the first sub-zone can be more easily separated.

According to the present invention, it is to be understood that the selection means and/or the drive means and/or the receiving means can at least partially be provided in the form of one single coil or solenoid. However, it is preferred according to the present invention that separate coils are provided to form the selection means, the drive means and the receiving means. Furthermore according to the present invention, the selection means and/or the drive means and/or the receiving means can each be composed of separate individual parts, especially separate individual coils or solenoids, provided and/or arranged such that the separate parts form together the selection means and/or the drive means and/or the receiving means. Especially for the drive means and/or the selection means, a plurality of parts, especially pairs for coils (e.g. in a Helmholtz or Anti-Helmholtz configuration) are preferred in order to provide the possibility to generate and/or to detect components of magnetic fields directed in different spacial directions.

According to the present invention, it is preferred that the drive means and/or the receiving means comprises at least partially a litz wire/stranded wire and preferably that the litz wire comprises a plurality of individual wires, each individual wire being surrounded by an electrically high resistive material. It is thereby possible to provide a very high current supporting surface inside the drive means and/or the receiving means which is important both for the case that an AC current with a comparably high frequency is to be supported and for the case that a DC current or an AC current having a comparably low frequency is to be supported by the drive means and/or the receiving means but in the presence of a static and/or an dynamic magnetic field that penetrates the drive means and/or the receiving means. According to the present invention, it is preferred that the litz wire is spun such that one individual wire is e.g. in the center of the litz wire at one position along the extension direction of the litz wire and that this individual wire is e.g. in the periphery of the litz wire at another position along the extension direction of the litz wire. Thereby it is possible that each one of all the individual wires is preferably provided such that, e.g. in a loop formed by the litz wire, the same impedance is realized by each individual wire. In still a further preferred embodiment of the present invention, the current supporting paths (e.g. the individual wires of the litz wire) are arranged such that the resistance in a given working frequency band and in a given electromagnetic field penetrating the current supporting paths is substantially minimal, i.e. dominated by thermal noise, especially generated by thermal noise due to the presence of the magnetic particles in the region of action, i.e. the resistance of the current supporting paths without the presence of an object (of examination) in the region of action is comparable or smaller than the resistance in presence of an object in the region of action. This is achieved in particular by means of carefully defining the individual current paths (e.g. individual wires), current strength, coil configuration and other characteristics of the current supporting paths of the selection means and/or of the drive means. Furthermore and in the case of current supporting paths in the form of litz wires, it is preferred that the litz wire has a ratio of the summed cross sectional area of the individual wires relative to the cross sectional area of the litz wire (filling factor) in a specified range and/or that the individual wires of the litz wire have a diameter of approximately 1 µm to approximately 50 µm, preferably of approximately 10 µm to approximately 25 µm. It is thereby possible to greatly enhance the used current supporting surface inside the litz wire and therefore to realise a reduced resistance of the overall configuration of the selection means and/or of the drive means and/or of the receiving means. Typically, the filling factor of the litz wire of the selection means and/or of the drive means is in the range of about 0.30 to about 0.70, preferably in the range of around 0.50, and therefore higher than the filling factor of the litz wire of the receiving means which is in the range of about 0.01 to about 0.20, preferably in the range of about 0.03 to about 0.10. Furthermore, the diameter of the individual wires of the litz wire of the selection means and of the drive means can be chosen higher than the diameter of the individual wires of the litz wire of the receiving means. According to the present invention, it is very advantageous to take into consideration a change in conducting properties of selection means or drive means if these means are penetrated by the magnetic field of each other. The resistance of the selection means, the drive means and/or the receiving means should be chosen as low as possible in the given environment or penetration pattern. The selection means and the drive means together are also called "field generator means". The selection means comprise magnetic field generation means that provide either a static (gradient) magnetic selection field and/or a comparably slowly changing long range magnetic selection field with frequencies in the range of about 1 Hz to about 100 Hz. Both the static part and the comparably slowly changing part of the magnetic selection field can be generated by means of a permanent magnet or by means of coils or by a combination thereof. The drive means comprise magnetic field generation means that provide a magnetic drive field with frequencies in the range of about 1 kHz to about 200 kHz or even to about 5 MHz, preferably about 10 kHz to about 100 kHz. At least part of the field generator means (i.e. the selection means and the drive means) can be implemented by discrete coils where the diameter of the current supporting path (or the individual wires in the case of litz wire) of each coil or of each field generator means has to be chosen in such a way that the skin effect does not increase the resistance of the coil.

The present invention further refers to a method for influencing and/or detecting and/or locating magnetic particles in a region of action, wherein the method comprises the steps of
generating a magnetic drive field so that the magnetization of the magnetic particles changes, wherein the magnetic particles comprise at least a first magnetic particle,
acquiring signals, which signals depend on the magnetization of the first magnetic particle in the region of action, the signals comprise at least a first signal generated by a first receiving probe and a second signal generated by a second receiving probe,
detecting signal features arising from the first magnetic particle in the first signal and in the second signal.

The advantage of such a method is that potentially a larger part of the region of action or the totality of the region of action can be taken into consideration continuously when conducting a measurement according to the inventive method.

Very preferably according to an embodiment of the present invention, the localization of the first magnetic particle depends on the amplitude of the signal features in both the first signal and the second signal. Very preferably the detection of the signal features is repeated for at least a second magnetic particle. In a further preferred embodiment of the present invention, the method further comprises the step of distinguishing in the time domain in the first signal and in the second signal magnetization responses related to the first magnetic particle and to the second magnetic particle respectively. This has the advantage that very flexible and dynamically adaptive measurements are possible according to the present invention.

It is furthermore preferred according to the present invention that the method further comprises the step of determining the spatial relationship of the first magnetic particle and the second magnetic particle. Thereby, a very precise location of the magnetic particles is possible.

Very preferably according to the present invention, the method comprises the step of generating a magnetic selection field having a pattern in space of its magnetic field strength such that a first sub-zone having a low magnetic field strength and a second sub-zone having a higher magnetic field strength are formed in the region of action. And in still a further preferred embodiment of the present invention, the location of the first magnetic particle and of the second magnetic particle is determined by analyzing the first signal and the second signal. Thereby, the inventive method is applicable both to situations where a comparably small number of magnetic particles are to be localized and to situations where a comparably large number of magnetic particles are to be localizes or analyzed.

The present invention further refers to the use of magnetic particles in an inventive arrangement or in method according to the present invention, where the magnetic particle shows a multidomain magnetic behavior and/or a ferromagnetic and/or a ferrimagnetic behavior. By the use of appropriate magnetic particles showing the property of deterministically providing a magnetization response due to a certain exterior magnetic field, it is possible to apply the inventive arrangement and the method according to the present invention to a large number of possible measurement scenarios.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

Figure 1:
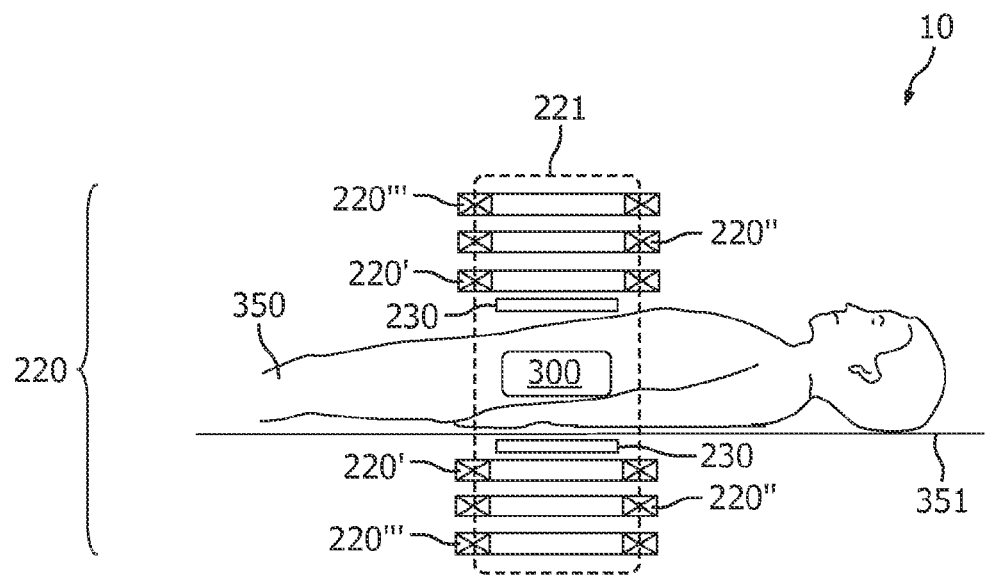
FIG. 1 illustrates schematically an arrangement according to the present invention for carrying out the method according to the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In FIG. 1, an arbitrary object to be examined by means of an arrangement 10 according to the present invention is shown. The reference numeral 350 in FIG. 1 denotes an object, in this case a human or animal patient, who is arranged on a patient table, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

According to the present invention, a so-called magnetic drive field 221 is generated in the region of action 300 by drive means 220. The magnetic drive field 221 is preferably variable in time, e.g., by means of an AC current in a coil of the drive means 220, for example with a sinusoidal variation. The magnetic particles 100 experience this magnetic drive field 221 inside the region of action 300.

In order to generate these magnetic drive fields 221 for any given direction in space, there are provided three coil pairs, namely a first coil pair 220', a second coil pair 220" and a third coil pair 220'" which together are called drive means 220 in the following. For example, the first coil pair 220' generates a component of the magnetic drive field 221 which extends in a given direction, i.e. for example vertically. To this end the windings of the first coil pair 220' are traversed by equal currents in the same direction. The two coil pairs 220", 220'" are provided in order to generate components of the magnetic drive field 221 which extend in a different direction in space, e.g. horizontally in the longitudinal direction of the region of action 300 (or the patient 350) and in a direction perpendicular thereto. If second and third coil pairs 220", 220'" of the Helmholtz type were used for this purpose, these coil pairs would have to be arranged to the left and the right of the region of treatment or in front of and behind this region, respectively. This would affect the accessibility of the region of action 300 or the region of treatment 300. Therefore, the second and/or third magnetic coil pairs or coils 220", 220'" are also arranged above and below the region of action 300 and, therefore, their winding configuration must be different from that of the first coil pair 220'. Coils of this kind, however, are known from the field of magnetic resonance apparatus with open magnets (open MRI) in which a radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein. According to the present invention, it is preferred that the resistance of the receiving means is dominated by thermal noise, especially generated by thermal noise due to the presence of the magnetic particles in the region of action, i.e. the resistance of the current supporting paths without the presence of an object (of examination) in the region of action is comparable or smaller than the resistance in presence of the object in the region of action. This is achieved in particular by means of carefully defining the individual current paths, current strength, wire configuration and other characteristics of the receiving means.

Figure 2:
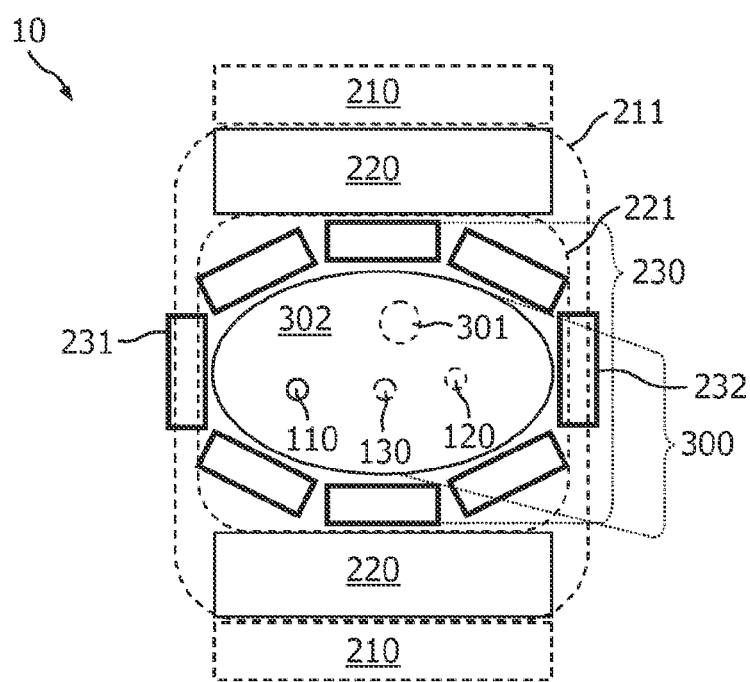
FIG. 2 illustrates schematically a further representation of an arrangement according to the present invention with more details of the region of action and the receiving means.

FIG. 2 schematically represents an arrangement 10 according to the present invention where the drive means 220 and the receiving means 230 are depicted schematically in relation to a schematical representation of the region of action 300 and three individual magnetic particles, namely a first magnetic particle 110, a second magnetic particle 120 and a third magnetic particle 130. The drive means 220 generates the magnetic drive field 221. In the example depicted in FIG. 2, the receiving means 230 comprise a first receiving probe 231 and a second receiving probe 232. These two receiving probes 231, 232, which are preferably realized by means of coils or solenoids, e.g. of litz wire, are described as being representatives for a plurality of receiving probes—commonly constituting the receiving means 230—which are not individually referred to by reference signs. Accordingly, the three magnetic particles 110, 120, 130 are described as being representatives for a plurality of magnetic particles which are not individually referred to by reference signs.

According to the present invention, the magnetic particles inside the region of action 300 experience the temporally changing magnetic drive field 220. This results in a change of the magnetization in the region of action 300. According to the present invention, each magnetic particle 110, 120, 130 to be localized or detected should be individually detected by means of the receiving means 230—in the present example by means of the first and second receiving probe 231, 232. This is possible if magnetic particles 110, 120, 130 are used such that a change in the external (magnetic drive) field 221 which is experienced by these particles 110, 120, 130 results in a more or less deterministic behavior of the magnetization response of each of the individual particles 110, 120, 130. This is explained in greater detail in connection with FIG. 3.

Figure 3:
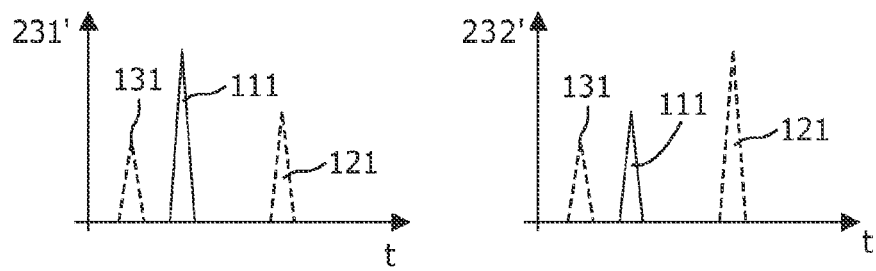
FIG. 3 illustrates schematically two examples of signals recorded by the receiving means comprising magnetization responses of particular magnetic particles.

In FIG. 3, on the left hand side, a diagram showing schematically the signal recorded by the first receiving probe 231 (in the time domain) comprising magnetization responses of the magnetic particles 110, 120, 130. On the right hand side, a diagram showing schematically the signal recorded by the second receiving probe 232 (in the time domain) comprising magnetization responses of the magnetic particles 110, 120, 130. The signal of the first receiving probe 231 is hereinafter called the first signal 231'. The signal of the second receiving probe 232 is hereinafter called the second signal 232'. The first signal 231' comprises the magnetization response of all the magnetic particles 110, 120, 130 present in the region of action 300 as seen by the first receiving probe 231. The second signal 232' comprises the magnetization response of all the magnetic particles 110, 120, 130 present in the region of action 300 as seen by the second receiving probe 232. The individual magnetization responses of the magnetic particles 110, 120, 130 are hereinafter called the first magnetization response 111 for the first magnetic particle 110, the second magnetization response 121 for the second magnetic particle 120 and the third magnetization response 131 for the third magnetic particle 130. As can be seen by comparing the diagrams of FIG. 3 for the first signal 231' and the second signal 232', the magnetization responses 111, 121, 131 differ depending upon by which one of the first and the second receiving probe 231, 232 they are recorded. For example, the first magnetization response 111 is stronger (higher peak and/or greater integral) in the first signal 231' than in the second signal 232'. This can be explained by the greater distance of the first magnetic particle 110 from the second receiving probe 232 than from the first receiving probe 231. Furthermore for example, the second magnetization response 121 is stronger (higher peak and/or greater integral) in the second signal 232' than in the first signal 231'. This can be explained by the greater distance of the second magnetic particle 120 from the first receiving probe 231 than from the second receiving probe 232. Therefore, according to the present invention, it is possible to deduce the spatial relationship of the first magnetic particle 110 and the second magnetic particle 120 relative to the receiving probes 231, 232 and/or relative to the arrangement 10. For a greater number of magnetic particles to be detected and/or to be located, the signals 231' and 232' become crowded by superposed magnetization responses of the multitude of particles to detect. Therefore, the invention also provides—optionally—the possibility to select a subset (hereinafter called first sub-zone) of the region of action 300 in order to reduce the number of magnetic particles that provide magnetization responses in the interesting part of the signals 231', 232'.

As an optional feature in connection with an arrangement 10 according to the present invention, FIG. 2 also depicts schematically selection means 210 (only delimited by a dashed line) that can serve to define in the region of action 300 a first sub-zone 301 of relatively low magnetic field strength and a second sub-zone 302 of higher magnetic field strength. In this optional embodiment of the inventive arrangement 10 (with the selection means 210), the first sub-zone 301 comprises a so-called field-free point. The selection means 210 generate a magnetic selection field 211 which is in general a gradient magnetic field which is represented in FIG. 2 schematically by a dashed line. It has a substantially constant gradient (e.g. in the direction of the (e.g. vertical) axis of a coil pair of the selection means 210) and reaches the value zero in the field-free point in the first sub-zone 301. Starting from this field-free point (not individually shown in FIG. 2), the field strength of the magnetic selection field 211 (if present) increases in all three spatial directions as the distance increases from the field-free point. Therefore—if the magnetic selection field 211 is activated—, more or less all of the magnetic particles inside the second sub-zone 302 (i.e. in the residual part of the region of action 300 outside of the first sub-zone 301 which is denoted by a dashed line around the field-free point) experience a relatively high field strength of the magnetic selection field 211 and therefore behave differently in the presence of the magnetic drive field 221 than without the activation of the magnetic selection field 211. Therefore, also the magnetization responses 111, 121, 131 of the magnetic particles 110, 120 and 130 are different if they are located in the second sub-zone 302 and if the magnetic selection field 211 is activated. The field-free point or first sub-zone 301 of the region of action 300 is preferably a spatially coherent area; it may also be a punctiform area or else a line or a flat area. By changing the position of the two sub-zones 301, 302 within the region of action 300, the (overall) magnetization in the region of action 300 changes. By measuring the magnetization in the region of action 300 or by measuring a physical parameters influenced by the magnetization, information about the spatial distribution of the magnetic particles in the region of action can be obtained in the manner as shown in connection with FIG. 3.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 10 kHz and approximately 100 kHz. The magnetic field variations that the receiving means are supposed to be sensitive are preferably in a frequency range of approximately 50 kHz to approximately 10 MHz.

Figure 4:
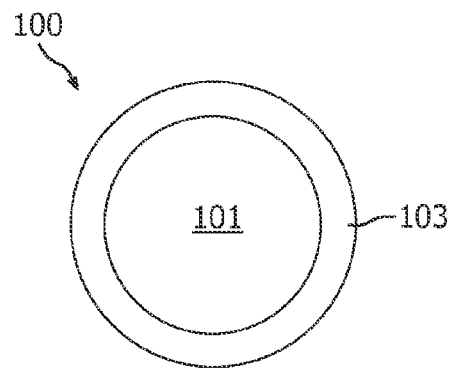
FIG. 4 illustrates schematically an enlarged view of a magnetic particle present in the region of action.

FIG. 4 shows an example of a magnetic particle 100 of the kind used together with an arrangement 10 of the present invention. It comprises for example a spherical magnetic material 101, for example, a sphere comprising Nickel or a Nickel alloy or comprising a magnetic steel. This magnetic material 101 may be covered, for example, by means of a coating layer 103 which protects the particle 100 against chemically and/or physically aggressive environments, e.g. acids. The magnetic field strength of the magnetic selection field 211 required for changing the behavior of the magnetization of such particles 100 is dependent on various parameters, e.g. the diameter of the particles 100, the used magnetic material and other parameters. Especially the use of magnetic particles providing the behavior of Barkhausen jumps when subjected to a changing external magnetic field are preferred according to the present invention, but other physical effects leading to distinguishable magnetization responses of the different magnetic particles can also be used according to the present invention.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

Figure 5:
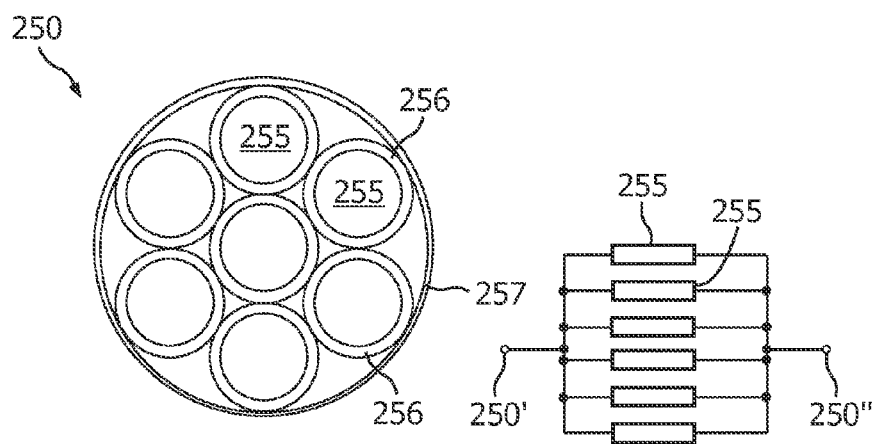
FIGS. 5 to 7 illustrate schematically different examples of litz wire configurations.
Figure 6:
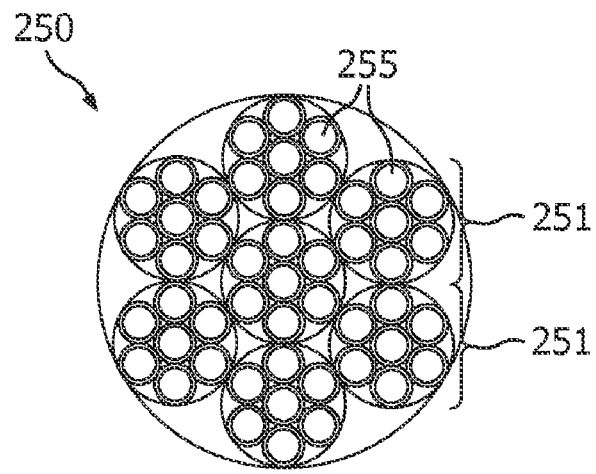
Figure 7:
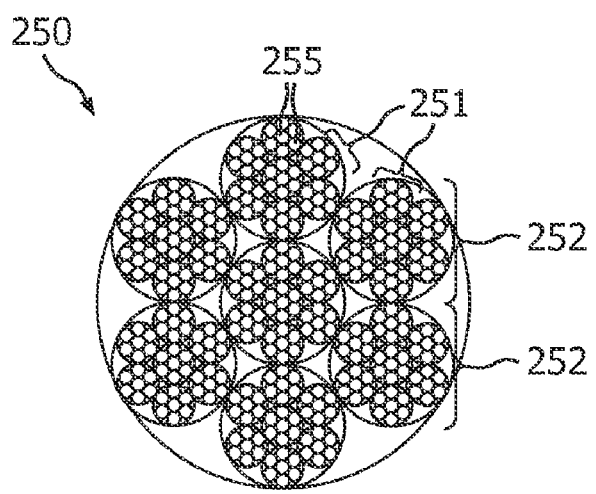

In FIGS. 5 to 7, litz wire 250 is shown in a schematical representation. The litz wire 250 is shown as one example to provide at least one current supporting path inside the selection means 210, the drive means 220 and/or the receiving means 230. Each of the FIGS. 5 to 7 represents a cross sectional view of one embodiment of such a litz wire 250. Each litz wire 250 comprises a multitude of individual wires 255. Thereby, an increase in current supporting surface is possible and the complexity of the handling requirements— especially the possibility of bending the litz wire (in order to form solenoids or coils) comprising a multitude of individual wires—are reduced. The representations of the various embodiments are not drawn to scale and the dimensions are chosen for the sake of representation simplicity only. The filling factor of the litz wire 250 can easily be evaluated by means of summing up the cross sectional areas of each of the individual wires 255 and dividing by the cross sectional area of the complete litz wire 250. By means of applying a pressure to the embodiments of the litz wire 250 represented in FIGS. 5 to 7 in a direction perpendicularly to the longitudinal extension of the litz wire 250, the filling factor can be enhanced. Each individual wire 255 is preferably surrounded circumferentially by an electrically high resistive material 256 which acts in the manner of a cladding 256 for each individual wire 255. It is to be understood that it is preferred according to the present invention that such a cladding material 256 is present at each individual wire 255; however such a continuous cladding 256 is not necessary if the condition is fulfilled that each individual wire 255 of the litz wire 250 is electrically isolated from the adjacent individual wires 250 between a first end 250' of the litz wire and a second end 250" of the litz wire 250. The individual wires 255 of the litz wire 250 act as individual current supporting paths 255 and can be regarded as resistors connected in parallel and having ideally an identical impedance as shown by the equivalent circuit diagram represented on the right hand side in FIG. 5. Therefore it is preferred according to the present invention, that the litz wire is spun such that one individual wire is e.g. in the center of the litz wire at one position along the extension direction of the litz wire and that this individual wire is e.g. in the periphery of the litz wire at another position along the extension direction of the litz wire. In the embodiment of the litz wire 250 represented in FIG. 5, a further preferred feature of the litz wire 250 is represented, namely a plastic foil insulation 257 is provided collectively around the individual wires 255. Such a plastic (e.g. thermoplastic) insulation can also be provided to all the other embodiments of the litz wire 250 but is not shown there. The additional feature of such an insulation foil or insulation material 257 collectively around the individual wires 255 of the litz wire 250 provides the advantage that a better high voltage performance of the litz wire is possible.

In FIG. 6 a cross sectional view of a further embodiment of the litz wire 250 is schematically shown where the litz wire 250 comprises also a plurality of individual wires 255 (as in the embodiment according to FIG. 5) but with the individual wires 255 grouped in a plurality of so-called first order litz wires 251. These first order litz wires 251 (each comprising a plurality of individual wires 255) are combined together to form the litz wire 250. In FIG. 6, the continuous cladding 256 is preferably present around each individual wire 255 but not indicated by means of a reference numeral.

In FIG. 7 a cross sectional view of a still further embodiment of the litz wire 250 is schematically shown where the litz wire 250 comprises also a plurality of individual wires 255 (as in the embodiments according to FIGS. 5 and 6) and a plurality of first order litz wires 251 but with the first order litz wires 251 grouped in a plurality of so-called second order litz wires 252. These second order litz wires 252 (each comprising a plurality of first order litz wires 251) are combined together to form the litz wire 250. In FIG. 6, the continuous cladding 256 is preferably present around each individual wire 255 but not represented for the sake of simplicity.

The invention claimed is:

1. An arrangement for at least one of influencing, detecting and locating magnetic particles in a region of action, wherein the arrangement comprises:
   a driver for generating a magnetic drive field so that a magnetization of the magnetic particles changes, wherein the magnetic particles comprise a first magnetic particle and a second magnetic particle;
   a receiver for acquiring signals that depend on the magnetization of the first magnetic particle in the region of action, wherein the receiver comprises at least a first receiving probe providing a first signal and a second receiving probe providing a second signal;
   a detector for determining signal features arising from at least one of the first magnetic particle in the first signal and in the second; and
   a signal processing unit configured to compare the first signal and the second signal to obtain information about a spatial relationship of the first magnetic particle and the second magnetic particle relative to the first receiving probe and the second receiving probe.

2. The arrangement according to claim 1, wherein localization of the first magnetic particle depends on an amplitude of the signal features in the first signal and in the second signal.

3. The arrangement according to claim 1, wherein localization of the second magnetic particle depends on an amplitude of the signal features in the first signal and in the second signal.

4. The arrangement according to claim 1, further comprising a selector for generating the magnetic selection field with a pattern in space of its magnetic field strength such that a first sub-zone having a low magnetic field strength and a second sub-zone having a higher magnetic field strength are formed in the region of action.

5. The arrangement according to claim 4, wherein the selector comprises at least partially a litz wire.

6. The arrangement according to claim 1, wherein at least one of the driver and the receiver comprises at least partially a litz wire.

7. The arrangement according to claim 1, wherein the receiver comprises a plurality of receiving probes.

8. An arrangement for at least one of influencing, detecting and locating magnetic particles in a region of action, wherein the arrangement comprises:
   a driver for generating a magnetic drive field so that the magnetization of the magnetic particles changes, wherein the magnetic particles comprise a first magnetic particle and a second magnetic particle;
   a receiver for acquiring signals that depend on the magnetization of the first magnetic particle in the region of action, wherein the receiver comprises at least a first receiving probe providing a first signal and a second receiving probe providing a second signal; and
   a detector for determining signal features arising from at least one of the first magnetic particle in the first signal and in the second signal,
   wherein the magnetization of the first magnetic particle and of the second magnetic particle is distinguishable due to Barkhausen jumps induced by the magnetic drive field or wherein the signal features of the first magnetic particle and of the second magnetic particle are due to Barkhausen jumps induced by the magnetic drive field.

9. An arrangement for at least one of influencing, detecting and locating magnetic particles in a region of action, wherein the arrangement comprises:
- a driver for generating a magnetic drive field so that the magnetization of the magnetic particles changes, wherein the magnetic particles comprise a first magnetic particle and a second magnetic particle;
- a receiver for acquiring signals that depend on the magnetization of the first magnetic particle in the region of action, wherein the receiver comprises at least a first receiving probe providing a first signal and a second receiving probe providing a second signal; and
- a detector for determining signal features arising from at least one of the first magnetic particle in the first signal and in the second signal,
- wherein the magnetization of the first magnetic particle and of the second magnetic particle is distinguishable in a time domain.

10. An arrangement for at least one of influencing, detecting and locating magnetic particles in a region of action, wherein the arrangement comprises:
- a driver for generating a magnetic drive field so that the magnetization of the magnetic particles changes, wherein the magnetic particles comprise a first magnetic particle and a second magnetic particle;
- a receiver for acquiring signals that depend on the magnetization of the first magnetic particle in the region of action, wherein the receiver comprises at least a first receiving probe providing a first signal and a second receiving probe providing a second signal; and
- a detector for determining signal features arising from at least one of the first magnetic particle in the first signal and in the second signal
- wherein the first receiving probe and the second receiving probe are positioned such that by comparing the first signal and the second signal, information about a spatial relationship of the first magnetic particle and the second magnetic particle relative to the first receiving probe and the second receiving probe is accessible.

11. A method for at least one of influencing, detecting and locating magnetic particles in a region of action, wherein the method comprises the acts of:
- generating a magnetic drive field so that a magnetization of the magnetic particles changes, wherein the magnetic particles comprise a first magnetic particle and a second magnetic particle;
- acquiring signals, that depend on the magnetization of the first magnetic particle in the region of action, wherein the signals comprise at least a first signal generated by a first receiving probe and a second signal generated by a second receiving, probe;
- detecting signal features arising from the first magnetic particle in the first signal and in the second signal; and
- comparing the first signal and the second signal to obtain information about a spatial relationship of the first magnetic particle and the second magnetic particle relative to the first receiving probe and the second receiving probe.

12. The method according to claim 11, wherein localization of the first magnetic particle depends on an amplitude of the signal features in both the first signal and the second signal.

13. The method according to claim 11 wherein localization of the second magnetic particle depends on an amplitude of the signal features in both the first signal and the second signal.

14. The method according to claim 11, further comprising the act of generating a magnetic selection field having a pattern in space of its magnetic field strength such that a first sub-zone having a low magnetic field strength and a second sub-zone having a higher magnetic field strength are formed in the region of action.

15. The method according to claim 11, wherein a location of the first magnetic particle and of the second magnetic particle is determined by analyzing the first signal and the second signal.

16. The use of magnetic particles in the arrangement according to claim 1 or in the method according to claim 11, the magnetic particle showing a multidomain magnetic behavior.

17. The use of magnetic particles in the arrangement according to claim 1 or in the method according to claim 11, the magnetic particle showing at least one of a ferromagnetic and a ferrimagnetic behavior.

18. A method for at least one of influencing, detecting and locating magnetic particles in a region of action, wherein the method comprises the acts of:
- generating a magnetic drive field so that a magnetization of the magnetic particles changes, wherein the magnetic particles comprise a first magnetic particle and a second magnetic particle;
- acquiring signals that depend on the magnetization of the first magnetic particle in the region of action, wherein the signals comprise at least a first signal generated by a first receiving probe and a second signal generated by a second receiving probe;
- detecting signal features arising from the first magnetic particle in the first signal and in the second signal; and
- distinguishing in the time domain in the first signal and in the second signal magnetization responses related to the first magnetic particle and to the second magnetic particle respectively.

19. A method for at least one of influencing, detecting and locating magnetic particles in a region of action, wherein the method comprises the acts of:
- generating a magnetic drive field so that a magnetization of the magnetic particles changes, wherein the magnetic particles comprise a first magnetic particle and a second magnetic particle;
- acquiring signals that depend on the magnetization of the first magnetic particle in the region of action, wherein the signals comprise at least a first signal generated by a first receiving probe and a second signal generated by a second receiving probe;
- detecting signal features arising from the first magnetic particle in the first signal and in the second signal; and
- determining a spatial relationship of the first magnetic particle and the second magnetic particle.

* * * * *